(12) United States Patent
Makeiff et al.

(10) Patent No.: US 9,017,701 B2
(45) Date of Patent: *Apr. 28, 2015

(54) ORGANOGEL COMPOSITIONS COMPRISING ALKYLATED BENZIMIDAZOLONES

(75) Inventors: Darren A. Makeiff, St. Albert (CA); Rina Carlini, Oakville (CA)

(73) Assignees: Xerox Corporation, Norwalk, CT (US); National Research Council of Canada, Ottawa (CA)

( * ) Notice: Subject to any disclaimer, the term of this patent is extended or adjusted under 35 U.S.C. 154(b) by 85 days.

This patent is subject to a terminal disclaimer.

(21) Appl. No.: 13/293,963

(22) Filed: Nov. 10, 2011

(65) Prior Publication Data

US 2013/0123375 A1 May 16, 2013

(51) Int. Cl.
*A61K 9/00* (2006.01)
*C07D 235/00* (2006.01)
*B01J 13/00* (2006.01)
*A61K 8/04* (2006.01)
*C07D 403/12* (2006.01)

(52) U.S. Cl.
CPC ............. *B01J 13/0065* (2013.01); *A61K 8/042* (2013.01); *C07D 403/12* (2013.01); *C08J 2205/024* (2013.01)

(58) Field of Classification Search
CPC .. C07D 403/12; C07D 417/12; C07D 405/12; C07D 235/22; C07F 9/65586; C04B 5/632; C07H 19/052
See application file for complete search history.

(56) References Cited

U.S. PATENT DOCUMENTS

| | | | | |
|---|---|---|---|---|
| 6,706,863 B2 * | 3/2004 | Hashimoto et al. | ............ | 534/742 |
| 7,503,973 B1 * | 3/2009 | Carlini | ........................ | 106/496 |
| 7,834,072 B2 * | 11/2010 | Carlini et al. | ................. | 524/157 |
| 7,857,901 B2 * | 12/2010 | Carlini et al. | .............. | 106/31.65 |
| 7,883,574 B2 | 2/2011 | Carlini et al. | | |
| 7,938,903 B2 | 5/2011 | Carlini et al. | | |
| 7,985,290 B2 * | 7/2011 | Carlini et al. | .............. | 106/31.78 |
| 8,025,723 B2 * | 9/2011 | Carlini et al. | .............. | 106/31.65 |
| 8,362,270 B2 * | 1/2013 | Makeiff et al. | ............ | 548/306.4 |
| 2008/0242773 A1 * | 10/2008 | Ushirogouchi et al. | ........ | 524/88 |
| 2010/0037955 A1 | 2/2010 | Carlini et al. | | |
| 2011/0292141 A1 * | 12/2011 | Sao et al. | ...................... | 347/100 |

FOREIGN PATENT DOCUMENTS

| | | | |
|---|---|---|---|
| CA | 002717579 A1 | * | 4/2011 |
| CN | 102040560 A | * | 5/2011 |
| EP | 2322512 A1 | * | 5/2011 |
| JP | 2011084552 A | * | 4/2011 |
| KR | 2011043419 A | * | 4/2011 |

OTHER PUBLICATIONS

Chemical Book (Pigment Yellow 180, Mar. 30, 2009, Wayback Machine).*
Shen et al (Nanostructures and Self-Assembly of Organogels via Benzimidazole/Benzothiazole Imide Derivatives with Different Alkyl Substituent Chains, 2013, Journal of Nanomaterials, vol. 2013, pp. 1-8).*
Makeiff et al., Copending U.S. Appl. No. 12/777,329, filed May 11, 2010.
Terech, P.; Weiss, R. G. Chem. Rev. 1997, 97, 3133-3159.
Hirst, A. R.; Escuder, B.; Miravet, J. F.; Smith, D. K. Angew. Chem. Int. Ed. 2008, 47, 8002-8018.
Herbstein, F. H., Kapon, M. Z. Kristallogr 1985, 173, 249-256.
Schwiebert, K. E.; Chin, D. N.; MacDonald, J. C.; Whitesides, G. M. J. Am. Chem. Soc. 1996, 118, 4018-4029.
K. Hunger, E. F. Paulus, D. Weber; Farbe & Lack, 1982, 88, 453.
E.F. Paulus; Zeit. Kristallographie; 1982, 160, 235.
Van De Streek, J., Brüning, J., Ivashevskaya, S. N., Ermrich, M., Paulus, E. F., Bolte, M., Schmidt, M. U. Acta Cryst. 2009, B65, 200-211.
Ebbing, M. H. K.; Villa, M.-J.; Valpuesta, J.-M.; Prados, P.; de Mendoza, J. Proc. Nat. Acad. Sci. 2002, 99, 4962-4966.

* cited by examiner

*Primary Examiner* — Brian-Yong Kwon
*Assistant Examiner* — Mark V Stevens
(74) *Attorney, Agent, or Firm* — Shimokaji IP

(57) ABSTRACT

Disclosed is a composition comprising an organogel which comprises: (a) an alkylated benzimidazolone compound; and (b) an organic liquid.

2 Claims, No Drawings

ORGANOGEL COMPOSITIONS COMPRISING ALKYLATED BENZIMIDAZOLONES

CROSS-REFERENCE TO RELATED APPLICATIONS

Reference is made to U.S. application Ser. No. 12/777,329, filed May 11, 2010, entitled "Self-Assembled Nanostructures," with the named inventors Darren Makeiff and Rina Carlini, the disclosure of which is totally incorporated herein by reference.

PARTIES TO A JOINT RESEARCH AGREEMENT

This application is a result of activities undertaken within the scope of a joint research agreement between Xerox Corporation and the National Research Council of Canada that was in effect on or before the date the research leading to this application was made.

BACKGROUND

Disclosed herein are organogel compositions comprising alkylated benzimidazolone compounds and organic liquids.

An organogel is a three-dimensional network of non-covalently interacting molecules with interstitial spaces filled by organic liquid. Low molecular weight organogels are a rapidly developing class of such materials, in which small molecular building blocks can self-assemble via non-covalent interactions (i.e., hydrogen bonding, pi-stacking, van der Waals, metal-ligand, or the like) into nano or microscale assemblies that can further organize into a three-dimensional network capable of rigidifying entire fluids at very low concentrations.

The "bottom up" self-assembly of molecular building blocks into nanostructured materials has attracted significant interest for advanced materials research. Nanostructured materials with controlled size, shape, and function are important for numerous industrial applications. Low molecular weight organogels are a rapidly developing class of such materials, in which small molecular building blocks self-assemble into hydrogen-bonded assemblies that can form a three-dimensional network capable of rigidifying entire fluids at very low concentrations. The use of organogel materials is diverse and spans many applications such as medicine, electronics, printing, personal care, and environmental remediation. Although a large number of organogelator compounds have been reported by many researchers, the rational design and synthesis of new organogelators remains a significant challenge since the gel properties in a given liquid cannot be predicted from the molecular structures alone. In addition, not all self-assembling nanostructures form gels when placed in contact with a liquid.

SUMMARY

Disclosed herein is a composition comprising an organogel which comprises: (a) an alkylated benzimidazolone compound; and (b) an organic liquid. Also disclosed herein is a composition comprising an organogel which comprises: (a) an alkylated benzimidazolone compound of the formula

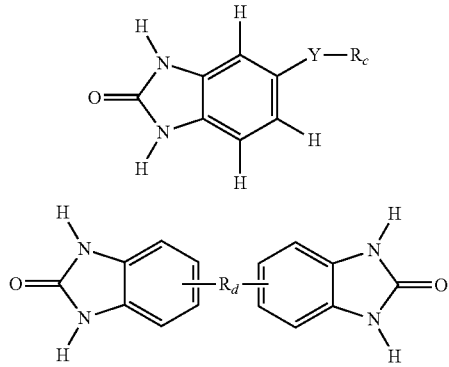

or wherein: (i) Y is: (A) —O—; (B) —S—; or (C) —NH—; (ii) $R_c$ is an alkyl group, including substituted and unsubstituted alkyl groups, wherein hetero atoms either may or may not be present in the alkyl group; and (iii) $R_d$ is a divalent moiety; and (b) an organic liquid. Further disclosed is a composition comprising an organogel which comprises: (a) an alkylated benzimidazolone compound of the formula

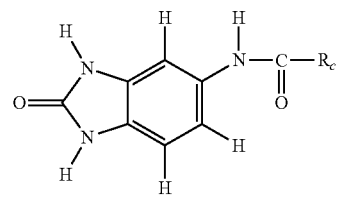

wherein $R_c$ is: (i) a branched unsubstituted alkyl group of the formula

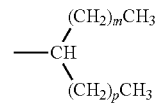

wherein m is an integer and p is an integer; (ii) a branched unsubstituted alkyl group of the formula

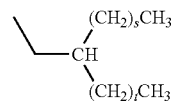

wherein s is an integer and t is an integer; (iii) a branched unsubstituted alkyl group of the formula

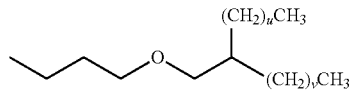

wherein u is an integer and v is an integer; or (iv) a multi-branched unsubstituted alkyl group of the formula

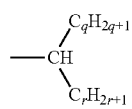

wherein q is an integer and r is an integer; and (b) an organic liquid.

DETAILED DESCRIPTION

The alkylated benzimidazolone compounds disclosed herein form gels by dissolution in an organic liquid with heating, and then cooling the resulting solution to result in gel formation. This process is attributable to the hierarchical self-assembly of the alkylated benzimidazolone molecules into a porous nanoscale gel network, which can entrap solvent molecules and rigidify the entire volume of liquid.

Heteroaromatic groups such as the benzimidazolone (BZI) group form reversible hydrogen bonds, resulting in the formation of oligomers or supramolecular polymers held together by non-covalent hydrogen bonds instead of covalent bonds. The BZI group is a conformationally restricted (rigid) cyclic urea fused to a benzene ring, which has strong hydrogen-bonding capability via two —NH donor groups and a lone —C=O acceptor group. Below are shown some examples of hydrogen bonding motifs for BZI derivatives, where association may occur via 2-point or 1-point hydrogen-bonding interactions, or combinations thereof:

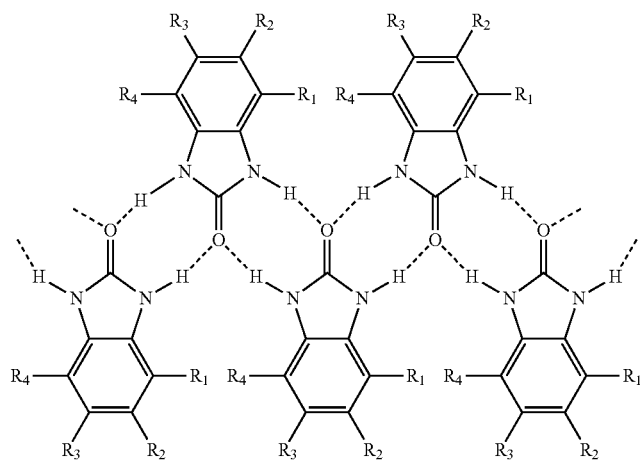

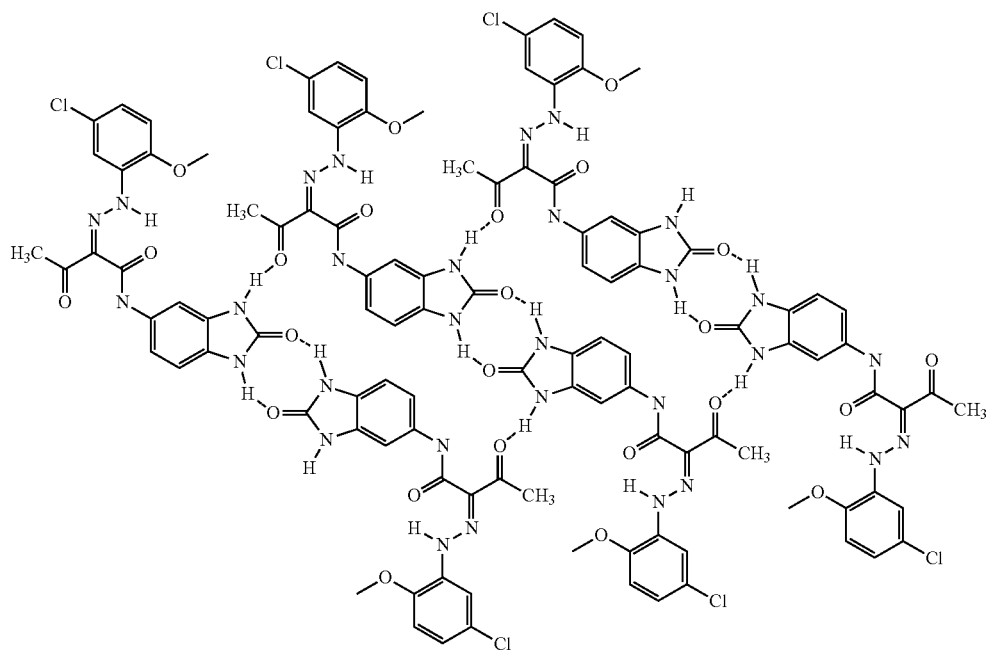

While many BZP compounds form hydrogen-bonded structures and self-assembling nanostructures, most of these structures are hard and highly crystalline in nature. The formation of soft organogels from such materials is of a different nature.

The organogels disclosed herein are formed with alkylated benzimidazolone compounds. These compounds include compounds of the formulae

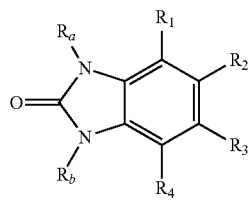

wherein:

$R_a$ and $R_b$ each, independently of the other, are (a) hydrogen atoms, or (b) alkyl groups, including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group, in one embodiment with at least about 1 carbon atom, in another embodiment with at least about 6 carbon atoms, and in yet another embodiment with at least about 12 carbon atoms, and in one embodiment with no more than about 100 carbon atoms, in another embodiment with no more than about 50 carbon atoms, and in yet another embodiment with no more than about 36 carbon atoms, although the number of carbon atoms can be outside of these ranges, provided that at least one of $R_a$ and $R_b$ is a hydrogen atom;

$R_1$, $R_2$, $R_3$, and $R_4$ each, independently of the others, are:

(a) hydrogen atoms;

(b) alkyl groups, including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group, in one embodiment with at least about 1 carbon atom, in another embodiment with at least about 6 carbon atoms, and in yet another embodiment with at least about 12 carbon atoms, and in one embodiment with no more than about 100 carbon atoms, in another embodiment with no more than about 50 carbon atoms, and in yet another embodiment with no more than about 36 carbon atoms, although the number of carbon atoms can be outside of these ranges;

(c) aryl groups, including substituted and unsubstituted aryl groups, and wherein hetero atoms, such as oxygen, nitrogen, sulfur, silicon, phosphorus, boron, or the like either may or may not be present in the aryl group, in one embodiment with at least about 5 carbon atoms, in another embodiment with at least about 6 carbon atoms, and in yet another embodiment with at least about 12 carbon atoms, and in one embodiment with no more than about 100 carbon atoms, in another embodiment with no more than about 50 carbon atoms, and in yet another embodiment with no more than about 36 carbon atoms, although the number of carbon atoms can be outside of these ranges, such as phenyl or the like;

(d) arylalkyl groups, including substituted and unsubstituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the arylalkyl group, in one embodiment with at least about 6 carbon atoms, in another embodiment with at least about 7 carbon atoms, and in yet another embodiment with at least about 12 carbon atoms, and in one embodiment with no more than about 100 carbon atoms, in another embodiment with no more than about 50 carbon atoms, and in yet another embodiment with no more than about 32 carbon atoms, although the number of carbon atoms can be outside of these ranges, such as benzyl or the like; or (e) alkylaryl groups, including substituted and unsubstituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the alkylaryl group, in one embodiment with at least about 6 carbon atoms, in another embodiment with at least about 7 carbon atoms, and in yet another embodiment with at least about 12 carbon atoms, and in one embodiment with no more than about 100 carbon atoms, in another embodiment with no more than about 50 carbon atoms, and in yet another embodiment with no more than about 32 carbon atoms, although the number of carbon atoms can be outside of these ranges, such as benzyl or the like;

provided that at least one of $R_1$, $R_2$, $R_3$, $R_4$, and $R_5$ is —X—$R_c$, wherein:

(f) —X— is a linking group between $R_c$ and the aromatic group, with examples including (but not being limited to):

(i) —O—;
(ii) —S—;
(iii) —SO—;
(iv) —SO$_2$—;
(v) —NH—(C=O)—;
(vi) —(C=O)—NH—;
(vii) —NH—(C=S)—;
(viii) —(C=S)—NH—;
(ix) —NH—;
(x) —NH—(C=O)—NH—;
(xi) —NH—(C=S)—NH—;
(xii) —NH—(C=O)—O—;
(xiii) —NH—(C=O)—S—;
(xiv) —O—(C=O)—NH—;
(xv) —S—(C=O)—NH—;
(xvi) —NH—(C=S)—O—;
(xvii) —NH—(C=S)—S—;
(xviii) —O—(C=S)—NH—;
(xix) —S—(C=S)—NH—;
(xx) —(C=O)—O—;
(xxi) —(C=O)—S—;
(xxii) —O—(C=O)—;
(xxiii) —S—(C=O)—;
(xxiv) —(C=S)—O—;
(xxv) —(C=S)—S—;
(xxvi) —O—(C=S)—;
(xxvii) —S—(C=S)—;
(xxviii) —O—(C=O)—O—;
(xxix) —O—(C=S)—O—;
or the like, as well as combinations thereof;

(g) $R_c$ is an alkyl group, including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group, in one embodiment with at least about 6 carbon atoms, in another embodiment with at least about 12 carbon atoms, and in yet another embodiment with at least about 18 carbon atoms, and in one embodiment with no more than about 100 carbon atoms, in another embodiment with no more than about 50 carbon atoms, and in yet another embodiment with no more than about 32 carbon atoms, although the number of carbon atoms can be outside of these ranges;

wherein two or more of $R_a$, $R_b$, $R_1$, $R_2$, $R_3$, and $R_4$ can be joined to form a ring;

wherein the substituents on the substituted alkyl, aryl, arylalkyl, and alkylaryl groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring.

The formula

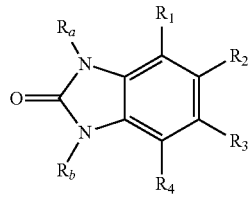

encompasses structures of the formula

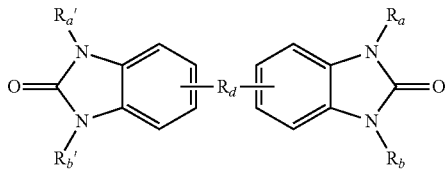

wherein $R_a'$ has the same definition as $R_a$ and can be either the same as or different from $R_a$, $R_b'$ has the same definition as $R_b$ and can be either the same as or different from $R_b$, and $R_d$ is a difunctional moiety that bridges two or more benzimidazole groups, with examples of suitable $R_d$ groups including (but not being limited to):

(a) —(CH$_2$)$_n$—;
(b) —X—(CH$_2$)$_n$—X'—;
(c) —[(XCH$_2$CH$_2$)$_n$]X'—;
(d) —[(C═O)—(CH$_2$)$_n$—(C═O)]—;
(e) —X—[(C═O)—(CH$_2$)$_n$—(C═O)]—X'—;
(f) —X—[(C═O)—X'—(CH$_2$)$_n$—X"—(C═O)]—X'"—;
(g) —[(C═O)—X—(CH$_2$)$_n$—X'—(C═O)]—;

or the like, wherein X, X', X", and X'" each, independently of the other, are defined as O, S, or NH, and n is an integer, in one embodiment at least about 1, and in one embodiment no more than about 50. Specific examples of $R_d$ also include large branched alkylated functional groups such as

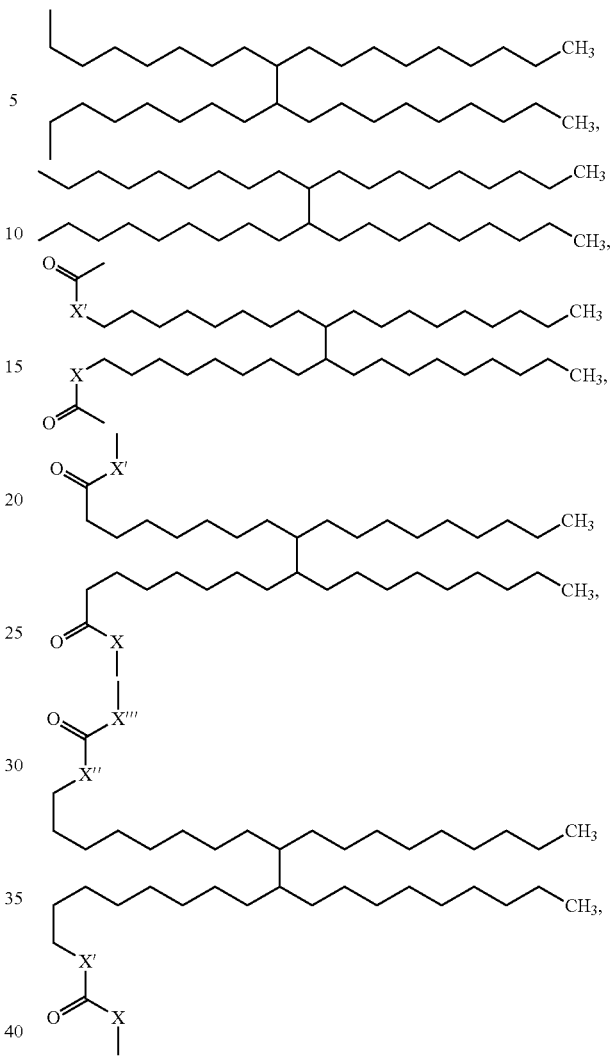

or the like, as well as mixtures thereof, wherein X, X', X", and X'" each, independently of the other, are defined as O, S, or NH.

In one specific embodiment, exactly one of $R_1$, $R_2$, $R_3$, $R_4$, and $R_5$ is —X—$R_c$.

In one specific embodiment, $R_2$ is —X—$R_c$ and $R_1$, $R_3$, and $R_4$ are hydrogen atoms. In another specific embodiment, $R_2$ is —X—$R_c$, $R_1$, $R_3$, and $R_4$ are hydrogen atoms, and $R_a$ and $R_b$ are hydrogen atoms.

In one specific embodiment, —X—$R_c$ is

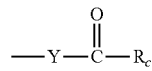

wherein —Y— is —O—, —S—, or —NH—. In another specific embodiment, —X—$R_c$ is

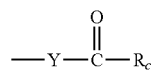

wherein —Y— is —NH—.

In one specific embodiment, the compound is of the formula
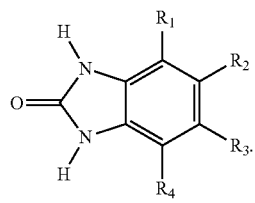
In another specific embodiment, the compound is of the formula
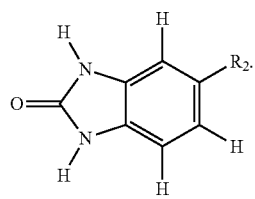
In yet another specific embodiment, the compound is of the formula
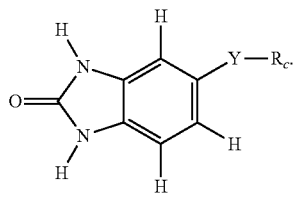
In still another specific embodiment, the compound is of the formula
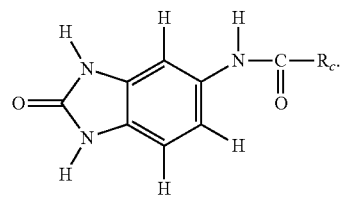
In one specific embodiment, the compound is of the formula
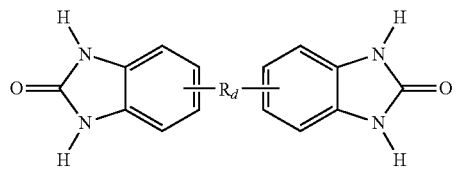
wherein $R_d$ is
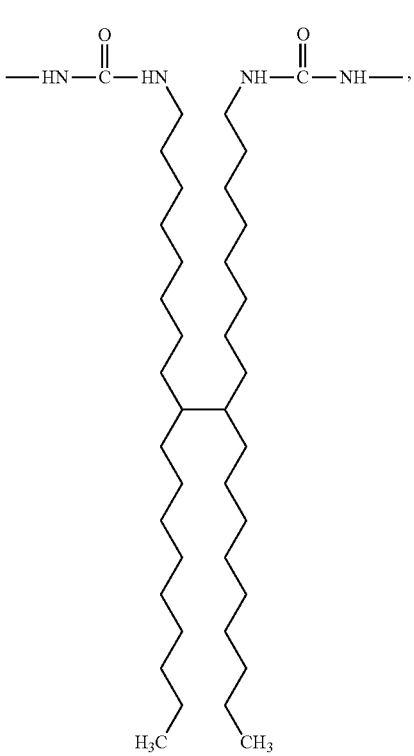
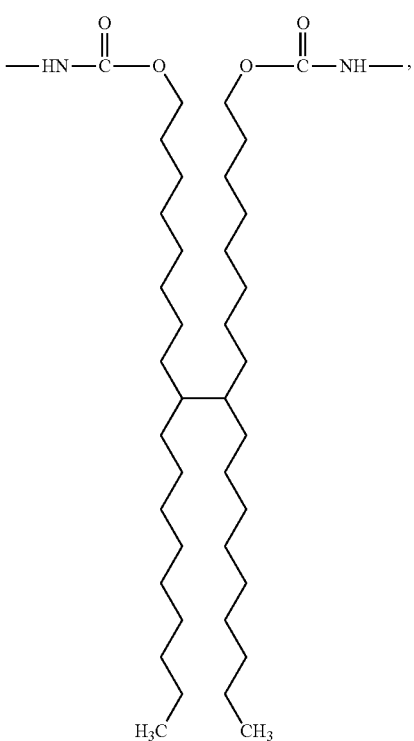

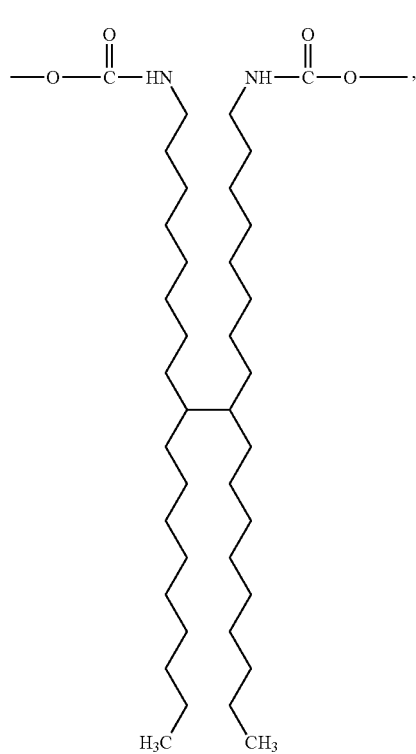
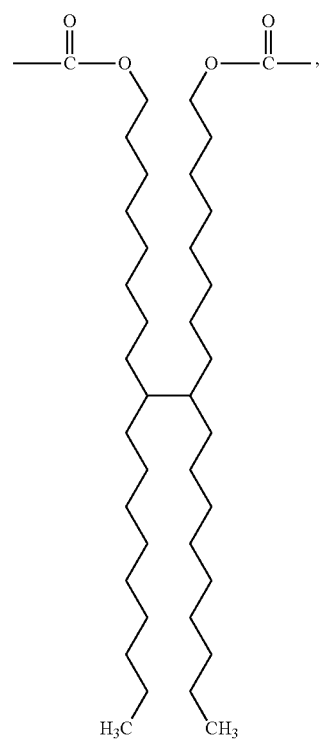
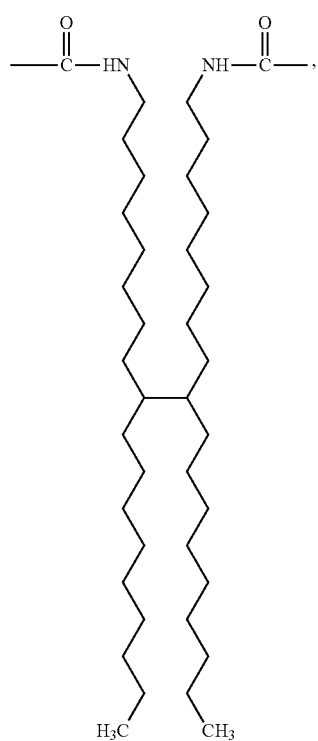
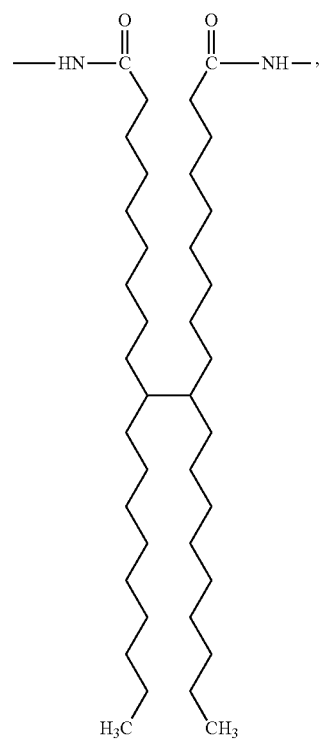

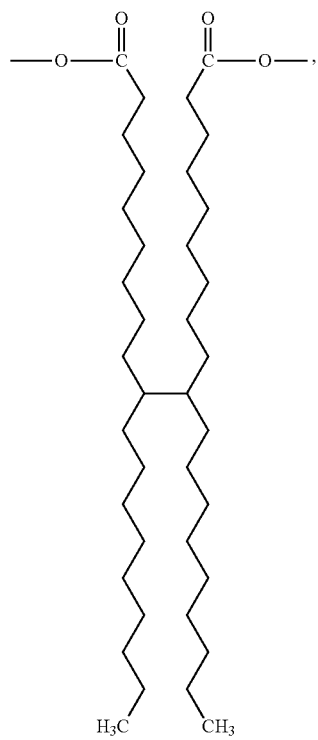
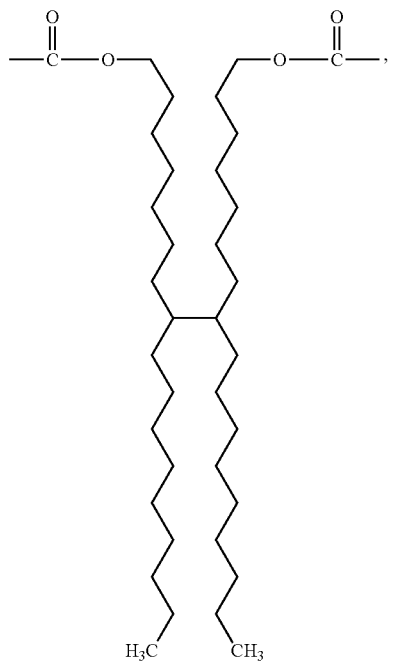
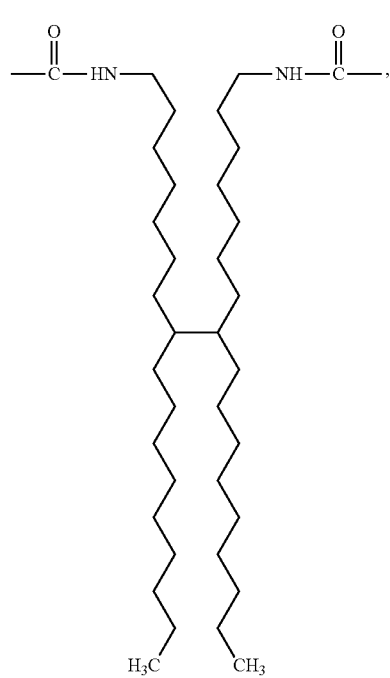
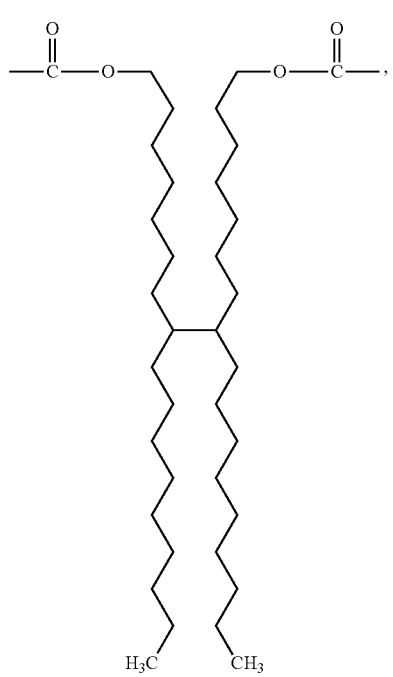

-continued

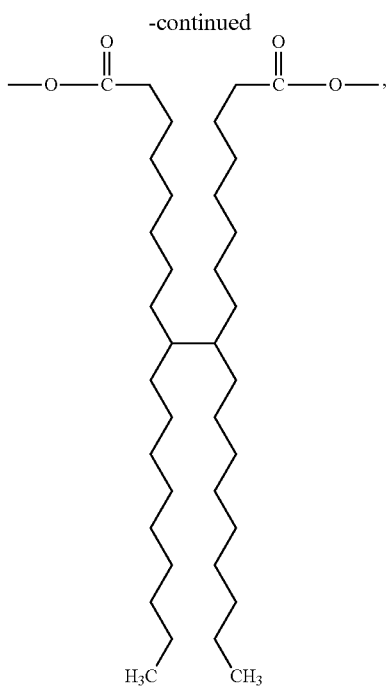

or the like, as well as mixtures thereof.

Specific examples of $R_c$ groups include (but are not limited to):

(a) branched unsubstituted alkyl groups of the formula

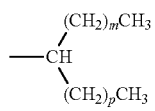

wherein m is an integer, in one embodiment 0, in another embodiment at least about 1, and in yet another embodiment at least about 3, and in one embodiment no more than about 17, in another embodiment no more than about 11, and in yet another embodiment no more than about 5, although the value of m can be outside of these ranges, and wherein p is an integer, in one embodiment 0, in another embodiment at least about 1, and in yet another embodiment at least about 3, and in one embodiment no more than about 17, in another embodiment no more than about 11, and in yet another embodiment no more than about 5, although the value of p can be outside of these ranges, including specific values such as:

(i) m=11, p=9;
(ii) m=7, p=5;
or the like;

(b) branched unsubstituted alkyl groups of the formula

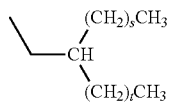

wherein s is an integer, in one embodiment 0, in another embodiment at least about 1, and in yet another embodiment at least about 3, and in one embodiment no more than about 49, in another embodiment no more than about 11, and in yet another embodiment no more than about 5, although the value of s can be outside of these ranges, and wherein t is an integer, in one embodiment 0, in another embodiment at least about 1, and in yet another embodiment at least about 3, and in one embodiment no more than about 59, in another embodiment no more than about 11, and in yet another embodiment no more than about 5, although the value of t can be outside of these ranges;

(c) branched unsubstituted alkyl groups of the formula

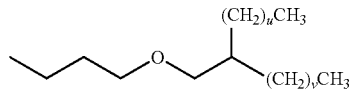

wherein u is an integer, in one embodiment 0, in another embodiment at least about 1, and in yet another embodiment at least about 3, and in one embodiment no more than about 49, in another embodiment no more than about 11, and in yet another embodiment no more than about 5, although the value of u can be outside of these ranges, and wherein v is an integer, in one embodiment 0, in another embodiment at least about 1, and in yet another embodiment at least about 3, and in one embodiment no more than about 59, in another embodiment no more than about 11, and in yet another embodiment no more than about 5, although the value of v can be outside of these ranges;

(d) multi-branched unsubstituted alkyl groups of the formula

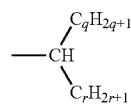

wherein q is an integer, in one embodiment at least about 1, in another embodiment at least about 4, and in yet another embodiment at least about 6, and in one embodiment no more than about 18, in another embodiment no more than about 12, and in yet another embodiment no more than about 10, although the value of q can be outside of these ranges, and wherein r is an integer, in one embodiment at least about 1, in another embodiment at least about 4, and in yet another embodiment at least about 6, and in one embodiment no more than about 18, in another embodiment no more than about 12, and in yet another embodiment no more than about 10, although the value of r can be outside of these ranges, including specific values such as:

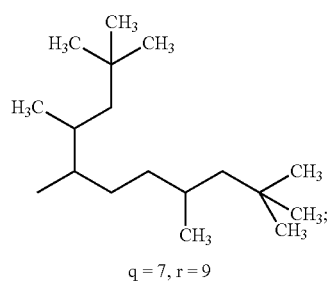

$q = 7, r = 9$

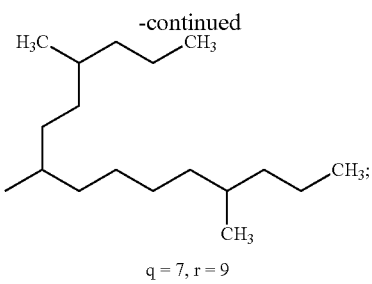

q = 7, r = 9 or the like, as well as mixtures thereof.

Alkylated benzimidazolone compounds can be prepared as disclosed in, for example, U.S. Pat. Nos. 7,503,973 and 7,938,903, and in Copending application U.S. Ser. No. 12/777,329, the disclosures of each of which are totally incorporated herein by reference.

The alkylated benzimidazolone compounds disclosed herein can be used to form organogels with an organic liquid. Any desired or effective organic liquid can be used, including (but not limited to) hydrocarbons, including aliphatic and aromatic hydrocarbons, alcohols, amines, esters, ethers, mercaptans, acids (including carboxylic acids, sulfonic acids, or the like, as well as mixtures thereof), sulfones, anhydrides, acid halides, siloxanes, polymeric liquids, ionic liquids, or the like, as well as mixtures thereof.

Specific examples of suitable organic liquids include (but are not limited to):

linear, branched, and/or cyclic unsubstituted aliphatic hydrocarbons, such as butanes, pentanes, such as n-pentane, isopentane, neopentane, cyclopentane, or the like, hexanes, such as n-hexane, isohexane, neohexane, cyclohexane, or the like, heptanes, such as n-heptane, isoheptane, neoheptane, cycloheptane, or the like, octanes, such as n-octane, isooctane, neooctane, cyclooctane, or the like, nonanes, decanes, such as n-decane, isodecane, neodecane, decadehydronaphthalene, or the like, undecanes, dodecanes, such as n-dodecane, isododecane, neododecane, or the like, tridecanes, tetradecanes, such as n-tetradecane, isotetradecane, neotetraadecane, or the like, pentadecanes, such as n-pentadecane, isopentadecane, neopentadecane, or the like, hexadecanes, such as n-hexadecane, isohexadecane, neohexadecane, or the like, heptadecanes, such as n-heptadecane, isoheptadecane, neoheptadecane, or the like, octadecanes, such as n-octadecane, isooctadecane, neooctadecane, or the like, nonadecanes, eicosanes, such as n-eicosane, isoeicosane, neoeicosane, or the like, naphthenes, or the like, as well as mixtures thereof;

linear, branched, and/or cyclic substituted aliphatic hydrocarbons, such as chloroform, carbon tetrachloride, 1,2-dichloroethane, or the like, as well as mixtures thereof;

linear, branched, and/or cyclic unsubstituted aliphatic alcohols, such as methanol, ethanol, propanols, butanols, pentanols, hexanols, heptanols, octanols, nonanols, decanols, undecanols, dodecanols, tridecanols, tetradecanols, pentadecanols, hexadecanols, heptadecanols, octadecanols, nonadecanols, eicosanols, or the like, as well as mixtures thereof;

unsubstituted aromatic and heteroaromatic hydrocarbons, such as benzene, toluene, xylenes, mesitylene, styrene, pyridine, pyrrole, furan, pyrazine, or the like, as well as mixtures thereof;

substituted aromatic and heteroaromatic hydrocarbons, such as fluorobenzene, chlorobenzene, bromobenzene, iodobenzene, nitrobenzene, or the like, as well as mixtures thereof;

aliphatic and aromatic amines, such as methyl amine, ethyl amine, propyl amine, butylamine, pentylamine, hexylamine, octylamine, decylamine, dodecylamine, octadecylamine, triethyl amine, diisopropyl ethyl amine, aniline, methyl anthranilate, or the like, as well as mixtures thereof;

aliphatic and aromatic esters, such as methyl acetate, ethyl acetate, butyl acetate, amyl acetate, methyl hexanoate, methyl octanoate, methyl myristate, methyl oleate, methyl linoleate, methyl benzoate, ethyl benzoate, benzyl benzoate, or the like, as well as mixtures thereof;

aliphatic and aromatic ethers, such as diethyl ether, dipropyl ethers, dibutyl ethers, dipentyl ethers, anisole, diphenyl ether, or the like, as well as mixtures thereof;

with examples of suitable substituents including (but not being limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring;

or the like, as well as mixtures thereof.

The alkylated benzimidazolone compound is present in the organic liquid in any desired or effective amount to form an organogel, in one embodiment at least about 0.05% by weight, in another embodiment at least about 0.1% by weight, and in yet another embodiment at least about 1% by weight, and in one embodiment no more than about 20% by weight, in another embodiment no more than about 10% by weight, and in yet another embodiment no more than about 5% by weight, although the amount can be outside of these ranges.

The organogel compositions disclosed herein can be used in a wide variety of applications, including (but not limited to) thickening agents for numerous products, such as paints, coatings, lubricants, adhesives, personal care products, pharmaceutical and dermatological gels, and even in certain food products, and they can be used in tissue engineering, biomineralization (as templates), catalysis, gel-based scaffolds for energy transfer and light harvesting, and the like.

Specific embodiments will now be described in detail. These examples are intended to be illustrative, and the claims are not limited to the materials, conditions, or process parameters set forth in these embodiments. All parts and percentages are by weight unless otherwise indicated.

The compounds in Examples I and II were used to gel organic liquids by the vial inversion method as described in, for example, Fages, F. *Low Molecular Mass Gelators*, Vol. 256, 2005 in Topics in Current Chemistry, the disclosure of which is totally incorporated herein by reference. Gels were prepared by placing a specified amount of gelator powder in a vial with an appropriate organic solvent. The mixtures were then heated to a specified temperature for a certain period of time until a homogeneous mixture or clear solution was obtained, followed by cooling and standing at room temperature for at least 30 min. The gels were then qualitatively evaluated using the "inversion test," which entailed inverting the gel sample and observing the flow behavior. If the material did not flow or fall under its own weight under gravity, the material was classified as a gel.

The minimum gelator concentration (MGC) is the minimum concentration of a gelator required to gel a liquid, usually expressed in weight %. The MGC can be determined by pre-weighing amounts of gelator and forming gels with the same amount of solvent followed by inversion test examination; alternatively, the gel can be successively diluted, reheated, cooled, and then examined by the inversion test.

The gel-sol transition temperature for the gelators were measured using the "dropping ball" method. In this method, a 2 mm stainless steel ball is carefully placed on top of a sample of gel in a sealed vessel. The gel is then slowly heated at a rate of about 1-2° C./min and the position of the ball is observed. The temperature at which the ball touches the bottom of the vessel is taken to be the gel-sol transition temperature. The gel-sol transition temperatures determined in this manner are dependent on other parameters, which are held constant, such as the total amount of organogel (organogelator and solvent), organogelator concentration, ball size/weight, and vessel dimensions.

Example I

Synthesis of 5-(2'-decyltetradecanamido)-2-benzimidazolone

Step 1: Preparation of 2-decyltetradecanoyl chloride

2-Decyltetradecanoic acid (ISOCARB 24, obtained from Sasol America, TX, 7.09 g, 0.0192 mol) and dry tetrahydrofuran (100 mL) were added to a 250 mL single-neck round-bottom flask under inert atmosphere. Oxalyl chloride (6.8 mL, 0.0779 mol, obtained from Sigma-Aldrich, Milwaukee, Wis.) was added dropwise, followed by a catalytic amount of N,N-dimethylformamide (0.30 µL, 3.87 mmol). The mixture was stirred for 30 min until gas evolution was observed to cease. The mixture was then stirred for an additional 90 min before the solvent was removed by rotary evaporation to afford a viscous, pale yellow oil. The acid chloride compound thus obtained was used in the next step without further purification.

Step 2: Preparation of 5-(2'-decyltetradecanamido)-2-benzimidazolone

5-Aminobenzimidazolone (2.93 g, 19.6 mmol, obtained from TCI America, Oregon, USA) and triethylamine (4 mL, 28.7 mmol) were dissolved in 20 mL N-methylpyrrolidinone in a 250 mL round-bottom flask under inert atmosphere. To this solution, a second solution of 2-decyltetradecanoyl chloride from Step 1 dissolved in dry THF (150 mL) was slowly added. After stirring overnight, deionized water was added and the mixture was poured into 300 mL ethyl acetate and washed with three 100 mL portions of deionized water. The organic layer was then concentrated by rotary evaporation until a white slurry was obtained. The solid was collected by filtration and washed with cold ethyl acetate to give 5-(2'-decyltetradecanamido)-2-benzimidazolone as a white solid (7.18 g). The product was identified by $^1$H and $^{13}$C NMR spectroscopy and ESI-MS and was of satisfactory purity. The compound was believed to be of the formula

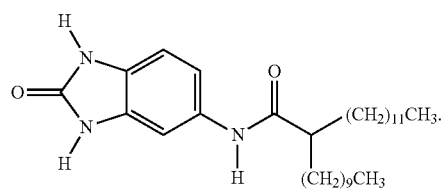

Gelation of Cyclohexane and Organogel Formation

The compound thus prepared was used for gelling cyclohexane. 5-(2'-Decyltetradecanamido)-2-benzimidazolone (41.7 mg) and cyclohexane (1 mL) were placed in a sealed vessel and mixed and heated until a clear, homogeneous solution was obtained. After slowly cooling and allowing the vessel to stand at room temperature for at least 30 min, a clear, transparent gel was formed, which did not fall or flow upon inverting the vessel.

Inversion tests were also repeated at varied concentrations of 5-(2'-decyltetradecanamido)-2-benzimidazolone in cyclohexane, and the MGC was determined to be 4.0 wt %.

Additional organogels were formed with 5-(2'-decyltetradecanamido)-2-benzimidazolone in other organic solvents. The results were as follows:

| Solvent | Appearance | MCG (wt. %) |
| --- | --- | --- |
| ethylene glycol | opaque gel | 0.1 |
| methanol | opaque gel | 0.9 |
| ethanol | opaque gel | 1.0 |
| 2-propanol | opaque gel | 0.9 |
| aniline | turbid gel | <4.0 |
| benzyl benzoate | turbid gel | 0.6 |
| cyclohexane | transparent gel | 0.4 |
| decalin | transparent gel | 0.4 |
| dodecane | turbid gel* | 0.2 |
| paraffin oil | turbid gel* | 0.3 |
| 2,2,4-trimethylpentane | turbid gel* | <5.0 |
| 1,2-dimethoxyethane | opaque gel | <2.0 |
| canola oil | turbid gel | 0.6 |

*= minor liquid phase separation occurred over time.

Determination of the Gel-to-Sol Transition Temperature

The "dropping ball" method was used to determine the gel-to-sol transition temperature for two of the above gels. A stainless steel ball (2 mm diameter) was carefully placed on the top of the gel formed from ~10 wt % 5-(2'-decyltetradecanamido)-2-benzimidazolone in cyclohexane. The vessel, a 1 dram vial with an outer diameter of 15 mm and a height of 45 mm, containing the gel was sealed and slowly heated in an oil bath at a rate of approximately 1-2° C./min. The ball touched the bottom of the vial at 45° C., which was taken to be the gel-to-sol transition temperature.

Example II

Synthesis of 5-(2'-hexyldecanamido)-2-benzmidazolone

Step 1: Preparation of 2-hexyldecanoyl chloride

2-Hexyldecanoic acid (JARCHEM, 6.61 g, 0.0258 mol, obtained from Jarchem Industries Inc., New Jersey, USA) and dry THF (50 mL) were added to a 250 mL single-neck round-bottom flask under inert atmosphere. Oxalyl chloride (9.0 mL, 0.103 mol, obtained from Sigma-Aldrich) was added slowly, dropwise, followed by a catalytic amount of DMF (0.30 mL, 3.87 mmol). The mixture was stirred for 30 min until gas evolution was observed to cease. The mixture was then stirred for an additional 90 min before the solvent was removed by rotary evaporation to afford a viscous mixture containing precipitates. The acid chloride compound thus obtained was used in the next step without further purification.

Step 2: Preparation of 5-(2'-hexyldecanamido)-2-benzmidazolone

5-Aminobenzimidazolone (3.86 g, 25.8 mmol, obtained from TCI America, Oregon, USA) and triethylamine (5.4 mL, 38.7 mmol) were dissolved in 20 mL N-methylpyrrolidinone in a 250 mL round-bottom flask under inert atmosphere. To this solution, a second solution of 2-hexyldecanoyl chloride from Step 1 dissolved in dry THF (50 mL) was slowly added. After stirring overnight, deionized water was added and the mixture was poured into 300 mL ethyl acetate and washed with three 100 mL portions of deionized water. The organic layer was then concentrated by rotary evaporation until a white slurry was obtained. The solid was collected by filtration and washed with cold ethyl acetate to give 5-(2'-hexyldecanamido)-2-benzmidazolone as a white solid (6.37 g). The product was identified by $^1$H and $^{13}$C NMR spectroscopy and ESI-MS and was of satisfactory purity. The compound was believed to be of the formula

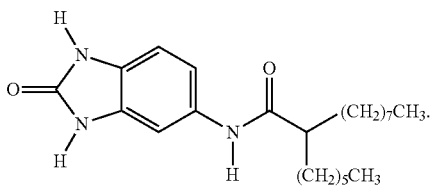

Gelation of Toluene and Organogel Formation 5-(2'-Hexyldecanamido)-2-benzmidazolone (29.9 mg) and toluene (1 mL) were placed in a sealed vessel and mixed and heated until a clear, homogeneous solution was obtained. After slowly cooling and allowing the vessel to stand at room temperature for at least 30 min, a turbid gel was formed, which did not fall or flow upon inverting the vessel.

Inversion tests were also repeated at varied concentrations of 5-(2'-hexyldecanamido)-2-benzmidazolone in toluene, and the MGC was determined to be between 2.5-3.0 wt %.

Additional organogels were formed with 5-(2'-hexyldecanamido)-2-benzmidazolone in other organic solvents. The results were as follows:

| Solvent | Appearance | MCG (wt. %) |
| --- | --- | --- |
| ethylene glycol | opaque gel | 0.2 |
| aniline | transparent gel | <5.0 |
| benzyl benzoate | turbid gel | 0.6 |
| cyclohexane | transparent partial gel | 10.0 |
| decalin | turbid gel | <2.5 |
| benzene | turbid gel | <4.0 |
| toluene | turbid gel | <3.0 |
| xylenes | turbid gel | <2.0 |
| mesitylene | transparent gel | <5.1 |
| styrene | turbid gel | <4.0 |
| dodecane | turbid gel | <11.0 |

Determination of the Gel-to-Sol Transition Temperature

The "dropping ball" method was used to determine the gel-to-sol transition temperature for 5-(2'-hexyldecanamido)-2-benzmidazolone in toluene. A stainless steel ball (2 mm diameter) was carefully placed on the top of the gel formed from ~3 wt % 5-(2'-hexyldecanamido)-2-benzmidazolone in toluene. The vessel, a 1 dram vial with an outer diameter of 15 mm and a height of 45 mm, containing the gel was sealed and slowly heated in an oil bath at a rate of approximately 1-2° C./min. The ball touched the bottom of the vial at 85° C., which was taken to be the gel-to-sol transition temperature.

Example III

Synthesis of bis-[5,5-(9',10'-dinonyloctadecanamido)-2-benzimidazolone]

Step 1: Synthesis of 9,10-dinonyloctadecanoyl dichloride 9,10-dinonyloctadecanoic acid (PRIPOL 1006, 3.44 g, 6.07 mmol) and dry THF (50 mL) were added to a 250 mL round-bottom flask under inert atmosphere and cooled to 0° C. Oxalyl chloride (3.20 mL, 36.7 mmol) was added slowly, dropwise, followed by DMF (0.140 mL, 1.81 mmol). The mixture was then slowly allowed to warm to room temperature and stirred for 3.5 h before the solvent was removed by rotary evaporation and dried in vacuo to give a pale yellow oil. The diacid chloride compound thus obtained was used in the next step without further purification.

Step 2: Synthesis of bis-[5,5-(9',10'-dinonyloctadecanamido)-2-benzimidazolone]

5-Aminobenzimidazolone (1.92 g, 12.8 mmol), triethylamine (2.5 mL, 1789 mmol), and dry N-methylpyrrolidinone (20 mL) were mixed in a 100 mL round-bottom flask under inert atmosphere. To this solution a second solution of 9,10-dinonyloctadecanoyl dichloride from Step 1 dissolved in dry THF (50 mL) was slowly added. After stirring overnight, deionized water (50 mL) was added to the beige suspension and the solid was collected by vacuum filtration and washed with deionized water to give bis-[5,5-(9',10'-dinonyloctadecanamido)-2-benzimidazolone] as a beige powder (4.87 g). The product was identified by $^1$H and $^{13}$C NMR spectroscopy and ESI-MS and was of satisfactory purity. The product was believed to be of the formula

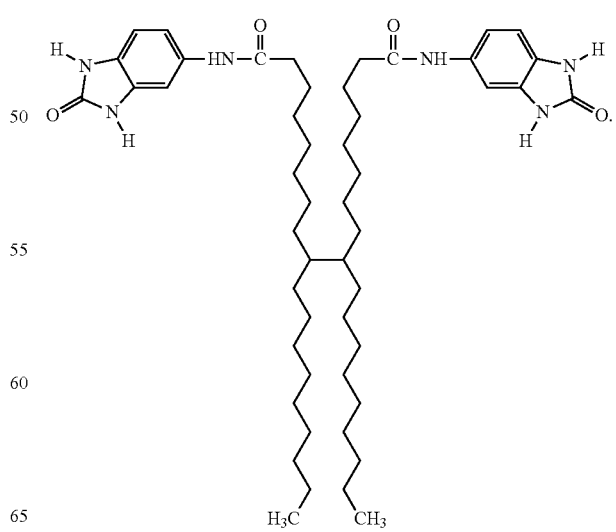

What is claimed is:

1. An organogel composition consisting of (a) an alkylated benzimidazolone compound of the formula

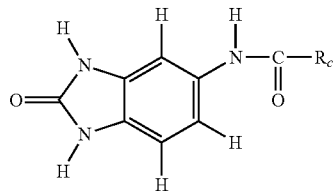

wherein $R_c$ is:
(i) a branched unsubstituted alkyl group of the formula

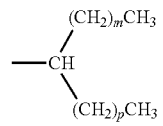

wherein m is an integer selected from the group consisting of integers from seven through eleven and p is an integer selected from the group consisting of integers from five through nine; and (b) an organic liquid, wherein the organic liquid is selected from the group consisting of ethylene glycol, methanol, ethanol, 2-propanol, aniline, benzyl benzoate, paraffin oil, 2,2,4-trimethylpentane, 1,2-dimethoxyethane, canola oil, benzene, mesitylene, and styrene.

2. The composition according to claim 1, wherein the alkylated benzimidazolone compound is present in the organic liquid in an amount from about 0.1 to about 10% by weight.

\* \* \* \* \*